(12) United States Patent
Pruche

(10) Patent No.: US 6,953,486 B2
(45) Date of Patent: Oct. 11, 2005

(54) DYEING COMPOSITION, METHOD FOR OBTAINING THE SAME AND USE FOR COLORING THE SKIN AND/OR KERATINOUS FIBRES

(75) Inventor: Francis Pruche, Senlis (FR)

(73) Assignee: L'Oreal, Paris (FR)

( * ) Notice: Subject to any disclaimer, the term of this patent is extended or adjusted under 35 U.S.C. 154(b) by 108 days.

(21) Appl. No.: 10/148,208

(22) PCT Filed: Oct. 9, 2001

(86) PCT No.: PCT/FR01/03110

§ 371 (c)(1), (2), (4) Date: Oct. 30, 2002

(87) PCT Pub. No.: WO02/30375

PCT Pub. Date: Apr. 18, 2002

(65) Prior Publication Data

US 2003/0163878 A1 Sep. 4, 2003

(30) Foreign Application Priority Data

Oct. 9, 2000 (FR) .................................. 00 12895
Oct. 9, 2000 (FR) .................................. 00 12894

(51) Int. Cl.⁷ .............................................. A61K 7/13
(52) U.S. Cl. ............................. 8/405; 8/94.14; 8/94.33; 8/628; 8/629; 424/70.1; 424/70.2; 424/70.4; 424/70.6; 132/202
(58) Field of Search ...................... 8/405, 94.15, 94.33, 8/628, 629, 406, 407, 410, 412, 424, 435, 594, 596, 600, 601; 424/70.1, 70.2, 70.4, 70.6; 132/202

(56) References Cited

FOREIGN PATENT DOCUMENTS

| EP | 0 335 403 | 10/1989 |
|---|---|---|
| GB | 917 840 | 2/1963 |
| GB | 2 024 623 | 1/1980 |
| JP | 53-133641 | 11/1978 |
| JP | 03-48612 | 3/1991 |
| JP | 3-48612 | 3/1991 |
| JP | 9-510226 | 10/1997 |
| JP | 2001-511436 | 8/2001 |
| JP | 2003-504447 | 2/2003 |
| JP | 2004-510796 | 4/2004 |
| WO | 92/20321 | 11/1992 |
| WO | WO 95/24886 | 9/1995 |
| WO | WO 99/06016 | 2/1999 |

OTHER PUBLICATIONS

Co–pending Application No. 10/000,222 Now U.S. Appl. No. 6,723,136 B2.
Co–pending U.S. Appl. No. 10/148,201 filed on Oct. 29, 2002.

*Primary Examiner*—Eisa Elhilo
(74) *Attorney, Agent, or Firm*—Oblon, Spivak, McClelland, Maier & Neustadt, P.C.

(57) ABSTRACT

Colouring composition, method for obtaining and using same for colouring skin and/or keratin matters.

The composition comprises, in a physiologically acceptable medium, an efficient amount of at least one colouring agent precursor selected among the compounds comprising at least one aromatic cycle having at least two hydroxyl groups carried by two consecutive carbon atoms of the aromatic cycle, optionally an amino acid comprising at least one thiol group and an efficient amount of a catalytic system comprising a first component selected amongst salts and oxides of Mn(II) and/or Zn(II) and/or the mixtures thereof and a second component selected amongst alkaline hydrogenocarbonates, alkaline earth hydrogenocarbonates and the mixtures thereof, the proportions of the first component and the second component being such that:

$$\frac{[Mn(II)]}{[HCO_3]} \leq 1 \quad \text{with} \quad [Mn(II)] \neq 0$$

$$\frac{[Zn(II)]}{[HCO_3]} \leq 1 \quad \text{with} \quad [Zn(II)] \neq 0$$

$$\frac{[Mn(II) + Zn(II)]}{[HCO_3]} \leq 1 \quad \text{with} \quad [Mn(II)] \text{ and } [Zn(II)] \neq 0$$

Application for colouring skin and/or keratin matters.

87 Claims, No Drawings

DYEING COMPOSITION, METHOD FOR OBTAINING THE SAME AND USE FOR COLORING THE SKIN AND/OR KERATINOUS FIBRES

The present invention generally relates to a colouring composition, more particularly for colouring skin and/or keratin fibres, a method for obtaining such a colouring composition and the use thereof for colouring skin and/or keratin fibres.

According to one embodiment, the present invention relates more particularly to a skin colouring composition which, after application on the skin, provides it with a homogeneous artificial tan and preferably with a complexion close to that of a natural tan.

In the field of colouring skin and/or keratin fibres, such as hair, eye-lashes, eye-brows and hairs, enzymatic catalysts are currently used nowadays in order to activate colouring the colouring precursors. Thus, the colouring of polyphenols is activated through oxidation in the presence of a natural polyphenoloxidase. By way of an example, catechin, in the presence of a natural polyphenoloxidase gives an orange yellow colouring and the dihydroxyphenylanaline (L. DOPA) gives melanin. The main advantage of such enzymatic catalysts consist in obtaining pigments with colours and original shades, without the use of oxidizing compounds. However, the main disadvantage of such a colouring method is the use of enzymes, for which the toxicological hazards, the stability in the compositions, the reproducibility, the price and the often required immobilization are factors significantly limiting their applications.

On the other hand, such catalysts are of protein nature and the use of proteins is not without risk for the use in beauty care or dermatology, including because of sensibilization reactions.

The use of enzymatic catalysts in the self-tanning type cosmetic preparations does not always afford a homogeneous colouring of the skin. The application on the whole body of dihydroxyacetone-containing compositions (or DHA), typically used in such type of application, is long and fastidious and obtaining a homogenous colouring is difficult.

In the field of tanning and self-tanning creams, an improvement has been obtained using, instead of enzymatic catalysts, chemical catalysts. For example, the WO 92/20321 A application discloses a tanning-enhancing cream for tanning light skins upon an exposition to the sun or to UVB rays, the composition of which comprises a sun screen, a physiologically acceptable medium and a pseudocatalase. The pseudocatalase is a coordination complex of a transition metal the metal of which is Cu(I), Fe(II) or Mn(II) and the ligand is a bicarbonate. It is meant by pseudocatalase a physiologically acceptable compound which catalyzes $H_2O_2$ dismutation in vivo as for a catalase.

For treating skin depigmentation associated to the transformation of tyrosin into melanine being blocked, such as for example vitiligo, the WO 92/20354 application discloses a composition containing, in a physiologically acceptable medium, a pseudocatalase.

Such pseudocatalase is a coordination complex of Fe(II), Cu(I) or Mn(II), the ligand being a bicarbonate.

The article by K. Schallreuter ("Pseudocatalase is a bis-manganese III-EDTA-(HCO3)2 complex activated by UVB or natural sun; J. Investing Dermator Symp Proc 1999 September; 451°; 91–6) mentions the use of a blend of sodium hydrogenocarbonate and manganese having an pseudocatalase activity for treating vitiligo. However, there is no indication, in those whole documents, relating to colouring.

In the field of capillary colouring, the European patent EP 621029 A discloses a composition comprising sodium chlorite, a hydrosoluble salt of Fe, Mn or Cu, or a chelate of such a salt and an oxidation colouring agent precursor.

Hair colouring requires using $H_2O_2$ ammonium or amine combinations.

There is therefore a need for colouring compositions, particularly for colouring skin and/or keratin fibres, which does not require using enzymatic systems.

The Applicant has discovered quite surprisingly that it is possible to obtain colouring compositions comprising at least one colouring agent precursor adapted to self-colour, in the presence of oxygen, through oxidation by means of an enzymatic system (oxidase) and, optionally, at least one amino acid comprising at least one thiol group (SH), by replacing the enzymatic system by a purely chemical system.

Thus, the chemical catalytic system of the invention behaves as a pseudo-oxidase able to simulate the oxidase activity without the inconvenients associated with the use of an enzymatic system.

The object of the present invention is therefore to provide a colouring composition, particularly for colouring skin and/or keratin fibres, which does not require the presence of enzymes.

The present invention also aims at a method for revealing the colouring of a basic composition, being somewhat or not coloured, comprising at least one colouring agent precursor through oxidation and optionally at least one amino acid comprising at least one thiol group consisting in adding to the basic composition a purely chemical catalytic system and in bringing the basic composition along with the catalytic system in the presence of an oxidizing medium such as a medium containing oxygen.

Another object of the present invention is also a method for obtaining a colouring composition such as defined hereabove.

The present invention additionally relates to a method for colouring skin and/or keratin fibres using a composition such as defined hereabove.

Finally, the present invention relates to packagings and galenical forms of the colouring composition or of components of the colouring composition according to the invention.

In the present invention, it is meant by cosmetic a product appealing to the senses with an appearance, a feel, an odour and a pleasant taste.

The composition for colouring skin and/or keratin fibres according to the invention comprises, in a physiologically acceptable medium, an efficient amount of at least one colouring agent precursor selected amongst compounds comprising at least one aromatic cycle having at least two hydroxyl groups (OH) carried by two consecutive carbon atoms of the aromatic cycle and an efficient amount of a catalytic system comprising a first component selected amongst salts and oxides of Mn(II) and/or Zn(II) and the mixtures thereof and a second component selected amongst alkaline hydrogenocarbonates, alkaline earth hydrogenocarbonates and the mixtures thereof, the proportions of the first component and the second component being such that:

$$\frac{[Mn(II)]}{[HCO_3]} \leq 1 \quad \text{with} \quad [Mn(II)] \neq 0$$

$$\frac{[Zn(II)]}{[HCO_3]} \leq 1 \quad \text{with} \quad [Zn(II)] \neq 0$$

$$\frac{[Mn(II) + Zn(II)]}{[HCO_3]} \leq 1 \quad \text{with} \quad [Mn(II)] \text{ and } [Zn(II)] \neq 0$$

where [Mn(II)], [Zn(II)] and [HCO_3] represent respectively the Mn(II), Zn(II) and $HCO_3$ molar concentrations in the composition.

Generally, the $$\frac{[Mn(II)]}{[HCO_3]}$$

ratio ranges from $10^{-5}$ to $10^{-1}$, preferably from $10^{-3}$ to $10^{-2}$ and is typically in the order of $5.10^{-3}$.

In the case of Zn(II), the $$\frac{[Zn(II)]}{[HCO_3]}$$

ratio is generally of an order of 10 to 100 times higher than the ratio in the case of Mn(II).

Typically, this ratio is $10^{-4}$ or more, preferably $10^{-3}$ or more, and more preferably in the order of $5.10^{-1}$.

In the case of a mixture of Mn(II) and Zn(II), the ratio ranges generally from $10^{-5}$ to $10^{-1}$, preferably from $10^{-3}$ to $10^{-2}$, this ratio being selected higher when the Zn(II) proportion in the mixture increases.

Mn(II) and Zn(II) salts appropriate for the present invention include chloride, fluoride, iodide, sulfate, phosphate, nitrate and perchlorate, the carboxylic acid salts and the mixtures thereof.

Examples include manganese chloride, manganese carbonate (for example, rhodochrosite), Mn(II) difluoride, Mn(II) tetrahydrated acetate, Mn(II) trihydrated lactate, Mn(II) phosphate, Mn(II) iodide, Mn(II) trihydrated nitrate, Mn(II) bromide, Mn(II) tetrahydrated perchlorate and Mn(II) monohydrated sulfate.

The particularly preferred salts are $MnCl_2$ and $ZnCl_2$.

The carboxylic acid salts also comprise hydroxylated carboxylic acid salts such as gluconate.

Alkaline and alkaline earth hydrogenocarbonates include Na, K, Mg, Ca hydrogenocarbonates and the mixtures thereof, preferably Na hydrogenocarbonate.

As previously stated, the chemical catalytic system according to the invention is a pseudo-oxidase in that it oxidizes the polyphenols, in the presence of oxygen, as a natural enzymatic catalyst with a polyphenoloxidase activity would do.

On the other hand, the catalytic system according to the invention has no pseudocatalase activity in the sense that it does not cause the dismutation of the hydrogen peroxide at 0.3% wt (i.e. 1 oxygen volume).

Moreover, the pseudo-oxidase activity is associated with the use of the catalytic system according to the invention. Accordingly, each of the catalytic system components, taken separately, has no pseudo-oxidase activity. Similarly, replacing a Mn (II) or Zn(II) salt by another salt, Fe, Cu or even Mn(II) does not lead to a catalytic system having a pseudo-oxidase activity.

The colouring agent precursors of the compositions of the invention are compounds or compound mixtures comprising at least one aromatic cycle, preferably a benzene cycle, comprising at least two hydroxyl groups (OH) carried by two consecutive carbon atoms of the aromatic cycle.

The aromatic cycle may be a condensed aromatic cycle optionally containing one or more heteroatoms, such as naphthalene, tetrahydronaphthalene, indane, indene, anthracene, phenanthrene, indole, isoindole, indoline, isoindoline, benzofurane, dihydrobenzofurane, chromane, isochromane, chromene, isochromene, quinoline, tetrahydroquinoline and isoquinoline.

The colouring agent precursors according to the invention can be represented by the formula:

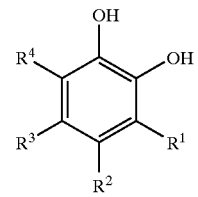
(I)

where the $R^1$ to $R^4$ substitutes, identical or different, represent a hydrogen atom, a halogen, hydroxyl, carboxyl, alkyl carboxylate radical, an optionally substituted amino radical, a linear or branched optionally substituted alkyl radical, a linear or branched optionally substituted alcenyl radical, a optionally substituted cycloalkyl radical, an alkoxy, alkoxyalkyl, alkoxyaryl radicals, the aryl group being able to be optionally substituted, aryl, substituted aryl, an optionally substituted heterocyclic radical, a radical containing one or more silicon atoms, where two of the components $R^1$ to $R^4$ jointly form a saturated or unsaturated cycle optionally containing one or more heteroatoms and optionally condensed with one ore more saturated or unsaturated cycles optionally containing one or more heteroatoms.

The saturated or unsaturated cycles, optionally condensed, can be also optionally substituted.

The alkyl radicals are generally $C_1$–$C_{10}$ alkyl radicals, preferably $C_1$–$C_6$ alkyl radicals, such as methyl, ethyl, propyl, butyl, pentyl and hexyl.

The alkoxy radicals are generally $C_1$–$C_{20}$ alkoxy radicals, such as methoxy, ethoxy, propoxy and butoxy.

The alkoxyalkyl radicals are preferably ($C_1$–$C_{20}$) alkoxy ($C_1$–$C_{20}$) alkyl, such as methoxymethyl, ethoxymethyl, methoxyethyl, ethoxyethyl, etc.

The cycloalkyl radicals are generally $C_4$–$C_8$ cycloalkyl radicals, preferably cyclopentyl and cyclohexyl radicals. The cycloalkyl radicals may be substituted cycloalkyl radicals, particularly substituted by alkyl, alkoxy, carboxylic acid, hydroxyl, amine and ketone groups.

The alcenyl radicals are preferably $C_1$–$C_{20}$ radicals, such as ethylene, propylene, butylene, pentylene, methyl-2-propylene and decylene.

The radicals containing one or more silicon atoms are preferably polydimethylsiloxane, polydiphenylsiloxane, polydimethylphenylsiloxane, steraoxydimethicone radicals.

The heterocyclic radicals are generally radicals comprising one or more heteroatoms selected amongst O, N and S, preferably O or N, optionally substituted by one or more alkyl, alkoxy, carboxylic acid, hydroxyl, amine or ketone groups.

The preferred heterocyclic radicals include the furyl, pyranyl, pyrrolyl, imidazolyl, pyrazolyl, pyridyl and thienyl groups.

Still more preferably, the heterocyclic groups are condensed groups such as benzofuranyl, chromenyl, xanthenyl, indolyl, isoindolyl, quinolyl, isoquinolyl, chromanyl, isochromanyl, indolinyl, isoindolinyl, coumarinyl, isocoumarinyl, such groups being optionally substituted particularly by one or more OH groups.

The preferred colouring agent precursors are:
flavanols such as catechin and epicatechin gallate,
flavonols such as quercetin,
anthocyanidins such as peonidin,
anthocyamins, for example, oenin,
hydroxybenzoates, for example gallic acid,
flavones such as luteolin,
iridoids, such as oleuropein.

such products being optionally osylated (for example glucosylated) and/or in the form of of oligomers (procyanidins);
hydroxystilbenes, for example tetrahydroxy-3,3',4,5'-stilbene, optionally osylated (for example glucosylated);
3,4-dihydroxyphenylalanine and the derivates thereof;
2,3-dihydroxyphenylalanine and the derivates thereof;
4,5-dihydroxyphenylalanine and the derivates thereof;
4,5-dihydroxyindole and the derivates thereof;
5,6-dihydroxyindole and the derivates thereof;
6,7-dihydroxyindole and the derivates thereof;
2,3-dihydroxyindole and the derivates thereof;
dihydroxycinnamates such as caefic acid and chlorogenic acid;
hydroxycoumarins;
hydroxyisocoumarins;
hydroxycoumarones;
hydroxyisocoumarones;
hydroxychalcones;
hydroxychromones;
anthocyans;
quinones;
hydroxyxanthones; and
the mixtures thereof.

When the colouring agent precursors exhibit D and L shapes, both shapes may be used in the compositions according to the invention.

By varying the nature of the different colouring agent precursors and their proportions in the composition, the final colouring composition colour can be varied. A colour range is thereby obtained.

For example, with a 1/10 ratio of chlorogenic acid to catechin, a light brown colouring is obtained and with a 1/1 ratio a mahogany colouring.

The polymers formed in particular with catechin, gallic acid and the derivates thereof (tannins) have antimicrobial properties through capture of the microorganisms upon polymerization. Such tannins also have astringent properties interesting for skin.

The colouring agent precursors can be plant, fruit, citrus fruit and vegetable extracts and mixtures of such extracts, containing numerous polyphenols, such as defined hereabove.

Plant extracts include rose and tea extracts.

Fruit extracts include apple, grape (more particularly grape seeds) and banana extracts.

Vegetable extracts include potato extract.

Mixtures of plant and/or fruit extracts may also be used, such as mixtures of appel and tea extracts and mixtures of grape and apple extracts.

Depending on the fruit parts being used, for example grape pulp or seeds, the resulting colouring is different.

The colouring agent precursor amount in the final composition should be sufficient so as to obtain a visible colouring. Such amount may vary in large extents depending on the nature of the precursor and on the desired intensity for colouring.

Generally, an appropriate colouring is obtained when the amount of colouring agent precursor is such that the colouring agent precursor content in the final colouring composition is at least 10 micromoles per milliliter of the final composition.

In a particular embodiment, the compositions according to the invention also contain an efficient amount of at least one amino acid comprising at least one thiol group.

In such embodiment, the preferred oxidation colouring agent precursors according to the invention are dihydroxyphenylalanines and the derivates thereof and dihydroxyindoles and the derivates thereof.

The amino acid comprises at least one thiol group (SH) and preferably only one thiol group, such an amino acid being optionally in the form of a hydrochloride.

The preferred amino acids according to the invention are amino acids containing an amine function in an α position relative to a carboxylic acid function.

The preferred amino acids can be represented by the formula:

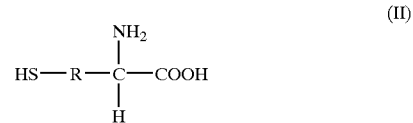

(II)

where —R is a divalent, linear or branched hydrocarbon radical, for example in $C_1$–$C_{10}$, preferably in $C_1$–$C_6$, such as a methylene, ethylene, butylene, ethylidene, propylidene radical, a divalent saturated cyclic radical, optionally substituted, for example in $C_4$–$C_8$, a divalent aromatic group, optionally substituted, such as a phenylene, tolylene or xylylene radical.

The preferred amino acids for the compositions of the invention include cysteine and the derivatives thereof, more particularly L-cysteine and L-cysteins hydrochloride, gluthatione and the derivates thereof.

The relative proportions of amino acid and oxidation colouring agent precursor in the compositions of the invention can vary in large extents depending on the desired colouring. Generally, the amino acid/colouring agent precursor molar ratio will range from 0.001 to 50, preferably from 0.01 to 5, more preferably from 0.05 to 2.5.

Generally, the content of amino acid having a thiol group in the final composition is at least 0.01 micromole per milliliter, preferably at least 0.1 micromole/ml.

Obviously, the doses of the components in the compositions of the invention are non toxic and compatible with beauty care.

By varying the nature of the colouring agent precursors and the amino acids in the composition and the relative proportion of amino acid and colouring agent precursor, a whole shade range can be obtained and particularly shades close to those of natural tan.

Thus, associating cysteine and dihydroxyindole makes it possible to obtain a brown shade, closer to that of a natural tan than using dihydroxyindole alone, which leads to an only black colour.

Such an association makes it possible to have a natural colouring of skin and hair, which is a mixture of eumelanine and pheomelanine in varying proportions.

The compositions of this particular embodiment of the invention may also lead to coloured films showing some transparency. Such a feature, associated to the fact that such compositions make it possible to obtain a shade close to natural tan, makes such compositions particularly interesting for application to the skin tan, making it possible to combine artificial tan and natural tan while obtaining a homogeneous shade.

The physiologically acceptable medium is a solid or liquid medium which does not damage the colouring property of the precursors nor the catalytic effect of the catalytic system.

The physiologically acceptable medium is preferably a solubilizing medium of the colouring agent precursor having a bacteriostatic property.

The precursor solvents appropriate for formulating the compositions according to the invention include desalted water, alcohols, polar solvents and the mixtures thereof.

The alcohols are preferably lower ($C_1$–$C_6$) alcanols such as ethanol and isopropanol and alcanediols such as ethylene glycol, propylene glycol and pentane diol.

The polar solvents include ethers, esters (particularly acetates), dimethylsulfoxide (DMSO), N-methylpyrrolidone (NMP), ketones (particularly acetone) and the mixtures thereof.

The physiologically acceptable medium comprises desalted water, preferably with a conductivity at temperature (25°) lower than or equal to 25 mΩ, for example water made and/or distributed by Millipore company under the designation milli Q, or a water/alcohol mixture, in particular water/ethanol.

The alcohol content in the water/alcohol mixture can represent up to 80% wt of the water/alcohol mixture, preferably 1 to 50% wt and more preferably 5 to 20% wt.

The physiologically acceptable medium can be a solid medium such as an excipient for formulating shingles and tablets, in particular effervescent ones.

The compositions according to the invention can also comprise any conventional builder, in a usual proportion, which does not damage the aimed properties, in particular the colouring effects of the compositions.

The compositions of the invention can, for example, comprise solar and UV protective screens, such as organic filters like benzophenone, benzylidene, triazine derivates, hydroxyphenyl benzotriazole derivates, cinnamic acid derivates, oxybenzone derivates, octocrylene, benzilidenecamphor derivates, and mineral filters such as ZnO, $TiO_2$.

When the compositions according to the invention comprise conventional pigments and colouring agents, they can be used for obtaining products such as foundation creams, the colouring action of which as exerted on the skin by the pigments and/or colouring agents is extended in time. Indeed, due to the friction in particular of the cheeks and the neck, a conventional foundation cream and, accordingly, the colouring effect thereof, tend to fade. Using a composition according to the invention in a foundation cream formulation would therefore make it possible to alleviate such effect.

Preferably, the compositions according to the invention are free of chelating agents of the Mn (II) and/or Zn (II) salts being used, as such agents tend to inhibit the oxidation of the colouring agent precursors.

In order to reveal the colouring of compositions according to the invention, the only thing to do is to put the composition containing at least one colouring agent precursor and an efficient amount of the catalytic system in the presence of an oxidizing medium, such as an oxygen-containing medium (for example oxygen from the air).

The compositions according to the invention are useful for colouring skin and/or keratin fibres such as hair, eyelashes, eye-brows and hairs. They can also be used for colouring food.

For colouring skin and keratin fibres, various application methods of the compositions according to the invention can be used.

According to one method, a composition comprising all the ingredients of the composition, i.e. both the colouring agent precursor(s) and the catalytic system is applied on skin or keratin fibres, in the presence of oxygen, for example oxygen from the air. The colouring is then revealed directly on skin or keratin fibres. Alternatively, the colouring of the composition can be revealed before the application thereof on skin or keratin fibres and the coloured composition can be applied on skin or keratin fibres.

According to a second method, a film of a basic composition of one or more colouring agent precursors in a physiologically acceptable medium can be first applied on skin or keratin fibres, and then, on the basic composition film, a catalytic system film in a physiologically acceptable medium is applied which, in the presence of oxygen, will reveal the colouring of the basic composition.

Obviously, the order of the film application can be inverted.

Film application can be performed using any known means, particularly by spraying.

Once the composition according to the invention is applied on skin and/or keratin fibres, a solution of one or more orthodiphenols can be applied, preferably different from those of the composition being applied, and, in so far as the initially present catalytic system has not been completely consumed, the addition of such (an) additional orthodiphenol(s) will increase the remanence of the colouring and/or, depending on the orthodiphenol(s) being used, will increase the intensity.

The compositions of the invention can, depending on the choice of the colouring agent precursors, make artificial tan compositions which, when sunscreens have been incorporated into them, provide skin with an artificially tanned appearance, while allowing a risk free exposure to the sun or the UV for a natural tan.

The compositions of the invention can also enable to conceal pigmentation defects such as vitiligo, chloasma, as well as skin imperfections such as aging marks and blotches.

The colouring of the composition can be determined by the choice of the colouring agent precursors and/or of the amino acid with a thiol group depending on the defect to be concealed.

The compositions of the invention have the advantage of not requiring the use of hydrogen peroxide.

The compositions according to the invention can have various forms and can be packed in different forms.

According to a first embodiment, the compositions according to the invention can be packed in the form of an aerosol with a single compartment containing the composition comprising the colouring agent precursor(s), optionally the amino acid(s), and the catalytic system and a conventional inert propellant such as nitrogen, a saturated hydrocarbon such as isopropane or a fluorinated hydrocarbon, for example a Freon®.

In a second embodiment, the composition according to the invention can be packed in the form of a kit comprising two discrete containers, one for the basic composition containing the colouring agent precursor(s) and optionally the amino acid(s), the other one for the catalytic system, the basic composition and the catalytic system being blended and applied successively in use.

In a third embodiment, the composition can be contained in a pump system with a single compartment, with no air absorption, or in a pump system with two compartments, the basic composition being in one compartment and the catalytic system in the other one.

In a fourth embodiment, the composition according to the invention can be present in the form of shingles, particularly for bath. Each shingle can comprise, blended with an excipient, the colouring agent precursor(s), optionally the amino acid(s), and the catalytic system, the excipient preventing the reaction in the presence of oxygen or the colouring agent precursor(s) and optionally the amino acid(s) and the catalytic system are contained in discrete shingles.

In cleaving either the single shingle or a shingle of each of the components in water, for example in the water of a bath, the colouring composition according to the invention is obtained.

The shingles, as it is conventional, may be effervescent shingles.

The excipient being used may be any conventional excipient such as a blend of talc, stearate (particularly magnesium stearate), citric and/or tartaric acid, and alkaline and/or alkaline earth hydrogenocarbonate.

The citric and/or tartaric acid amount being present should be such as to avoid any neutralization of the hydrogenocarbonate resulting in a lack of free hydrogenocarbonate relative to Mn(II) and/or Zn(II).

On the other hand, as water, in particular tap water and some spring or mineral waters, generally contains manganese (II), it is sometimes sufficient to put into water the single shingle containing hydrogenocarbonate and the colouring agent precursor(s), the Mn(II) content of the catalytic system being then supplied by the Mn(II) present in water.

Similarly, some plant extracts (for example tea extracts) can contain large manganese (II) amounts. Depending on these contents, a concentration adjustment of the catalytic system is carried out so as to obtain a satisfactory result.

Obviously, the colouring intensity can be varied in cleaving several shingles in water.

Additionally, the colouring speed can be accelerated adding to the composition a compound or a formulation of oxygen-generating compounds, for example, by contact with water. Thus, such compound or such formulation can be incorporated, for example, sodium peroxide, into a shingle.

The following examples illustrate the present invention. In the examples, unless otherwise indicated, all percentages and parts are expressed in weight.

EXAMPLE 1

Several colouring composition formulations have been prepared by varying the [$MnCl_2$]/[$NaHCO_3$] molar ratio of the catalytic system. The formulations are given in table I hereunder:

TABLE I

| | Colouring agent precursor | | Physiologically acceptable medium | Catalytic system | | |
|---|---|---|---|---|---|---|
| Formulation n° | Nature | Concentration (mM/l) | | $MnCl_2$ $NaHCO_3$ ratio | $MnCl_2$ concentration (mM/l) | $NaHCO_3$ concentration (mM/l) |
| 1 | Catechin | 1 | Saline solution with | $10^{-3}$ | $10^{-2}$ | 10 |
| 2 | Catechin | 1 | Dulbecco (PBS) | $2.5 \cdot 10^{-3}$ | $2.5 \cdot 10^{-2}$ | 10 |
| 3 | Catechin | 1 | phosphate buffer | $5 \cdot 10^{-3}$ | $5 \cdot 10^{-2}$ | 10 |
| 4 | Catechin | 1 | either in g/l: | $10^{-2}$ | $10^{-1}$ | 10 |
| 5 | L-DOPA | 1 | $KH_2PO_4$:0.2 | $10^{-3}$ | $10^{-2}$ | 10 |
| 6 | L-DOPA | 1 | $MnCl_2$:0.2 | $2.5 \cdot 10^{-3}$ | $2.5 \cdot 10^{-2}$ | 10 |
| 7 | L-DOPA | 1 | NaCl:8.0 and | $5 \cdot 10^{-3}$ | $5 \cdot 10^{-2}$ | 10 |
| 8 | L-DOPA | 1 | $Na_2HPO_4$:1.15 and 10% wt ethanol | $10^{-2}$ | $10^{-1}$ | 10 |

The maximum speeds (Vmax) at air colouring of the above-mentioned formulations are measured. The maximum speed is the optical millidensity increase (mDo) per minute on the kinetics area in which such speed is maximum. A measurement is made every minute and Vmax is determined on 8 points during the first 40 minutes. The optical density readings have been made at 475 nm with a Labsystem iEMS optical density reader.

The results are given in table II hereunder:

TABLE II

| Formulation n° | Vmax |
|---|---|
| 1 | 135 |
| 2 | 155.8 |
| 3 | 177.8 |
| 4 | 158 |
| 5 | 38.3 |
| 6 | 48.8 |
| 7 | 61 |
| 8 | 55.8 |

EXAMPLE 2

Several 500 µl samples have been prepared of colouring composition formulations according to the invention containing an amino acid with a thiol group as well as a 500 µm sample of a comparative formulation which does not contain any amino acid with a SH group.

The formulations are given in table III hereunder:

TABLE III

| | FORMULATIONS | | | | | |
|---|---|---|---|---|---|---|
| | Comparative A | 9 | 10 | 11 | 12 | 13 |
| L-DOPA | 5 mM/l | 5 mM/l | 5 mM/l | 5 mM/l | 5 mM/l | 5 mM/l |
| L-cysteine | — | 200 µM/l | 1 mM/l | 2 mM/l | 5 mM/l | 10 mM/l |
| Catalytic system | | | | | | |
| $MnCl_2$ | 0.5 mM/l | 0.5 mM/l | 0.5 mM/l | 0.5 mM/l | 0.5 mM/l | 0.5 mM/l |
| $NaHCO_3$ | 0.5 M/l | 0.5 M/l | 0.5 M/l | 0.5 M/l | 0.5 M/l | 0.5 M/l |
| EtOH | 10 µl | 10 µl | 10 µl | 10 µl | 10 µl | 10 µl |
| Water qsp | 500 µl | 500 µl | 500 µl | 500 µl | 500 µl | 500 µl |

L-DOPA and L-cysteine are introduced in the formulations in the form of solutions in ethanol (100 mM/l).

The catalytic system is introduced in the form of an aqueous solution (250 µl).

The absorption spectra of the above-mentioned formulations have been determined using a Perkin-Elmer lambda 2 spectrometer.

The absorption spectra are shown in FIG. 1. It can be seen that adding L-cysteine in the formulations shifts the absorption spectrum towards the orange yellow colour.

EXAMPLE 3

This example shows the influence of a tea extract with a high polyphenol content on the remanence of the products resulting from the reaction mixture (L-Dopa+L-cysteine+$MnCl_2$+$ZnCl_2$+sodium bicarbonate+$H_2O$=composition A).

To this end, a carrier (V) is used, which is a blend of solvents (ethanol/isopropanol/propylene glycol/urea) (32.3/32.3/32.4/3).

Preparation of Composition 5A

A first solution is prepared separately comprising:

| | |
|---|---|
| L-Dopa | 200 mg |
| L-cystein | 350 mg |
| $MnCl_2$ | 200 mg |
| $ZnCl_2$ | 130 mg |
| $H_2O$ | qs 25 ml | and a second solution is prepared:

| | |
|---|---|
| Sodium bicarbonate | 2,1 g |
| $H_2O$ | qs 25 ml |

The first solution is poured into the second solution so as to obtain the composition A.

500 mg sodium peroxide are then added to the blend.

It is left in the air for 24 hours ($A_{24H}$) under stirring, and then packed under argon.

Preparation of the Tea Extract

One blends:

| | |
|---|---|
| Green tea 95 | 1 g |
| Ethanol | qsp 10 ml |

In Vivo Assay

Several preparations are made using the above-mentioned active ingredients. The detail of the preparations being made is shown in table IV hereunder.

The composition A, the carrier and the tea extract are blended extemporaneously before application on skin.

The amounts present in the extemporaneous preparation are as follows:

composition A: 1 ml carrier: 1,5 ml alcohol tea extract: 100 µl

When the tea extract is not present, it is replaced by the carrier.

The selected application site is the forearm. 2.5*2.5 $cm^2$ squares are drawn on the skin. The colourimetric measurements have been performed using a CR-508d Minolta spectrocolourimeter.

The results are expressed in the (L*, a*, b*) system in which L* represents luminance, a* represents the red-green axis (−a*=green, +a*=red) and b* represents the yellow-blue axis (−b*=blue, +b*=yellow). Thus, a* and b* express the skin shade.

DE expresses the colour differences before and after the compositions are applied, either before a bath, or after a bath.

The colourimetric measurements are performed according the following sequence:

T=0 measurement of the non coloured skin

T=5 minutes, composition application at 4 mg/$cm^2$

T=3 hours, coloured skin reading (a 3 hours period has been chosen arbitrarily in this preliminary trial)

T=3 hours and five minutes, one minute bath in water at 28° C.

T=3 hours and fifteen minutes, air drying and measurement of the coloured skin colour.

TABLE IV

| Composition | Applied amount | Before bath | | | | After bath | | | | ΔE % loss between |
|---|---|---|---|---|---|---|---|---|---|---|
| | | L* | a* | B* | DE before bath♦ | L* | a* | b* | DΔ after bath♦♦♦ | before and after bath |
| V $A_{24H}$ tea | 4 mg/$cm^2$ | 57.99 | 11.88 | 20.24 | 9.29 | 59.12 | 10.33 | 15.32 | 4.61 | 50.4 |
| V $A_{24H}$ | 4 mg/$cm^2$ | 61.45 | 8.96 | 18.79 | 6.65 | 62.12 | 8.47 | 13.96 | 2.13 | 68.0 |

V: carrier
A: products resulting from the reaction blend (L-Dopa + L cysteine + $MnCl_2$ + $ZnCl_2$ + sodium bicarbonate + $H_2O$)
Tea: tea extract (green tea 95)
♦the DE expresses the colour differences before and after application of the products, before bath
♦♦the DE expresses the colour differences before and after application of the products, after bath Adding tea to preparation $A_{24H}$ makes it possible to obtain a more vivid and slightly more red colour.

Preparation $A_{24H}$ alone has a rather significant colour loss % (DE loss % in the order of 68).

Adding tea to preparation $A_{24H}$ makes it possible to obtain a colour loss reduction (the DE loss is reduced from 68 to 50.4%).

Adding tea makes it possible to increase the colour remanence of the products resulting from the reaction blend (L-Dopa+L cysteine+$MnCl_2$+$ZnCl_2$+sodium bicarbonate+$H_2O$).

The colouring compositions according to the invention offer numerous advantages in the field of skin and hair colouring. For example, the behaviour on the skin is reinforced because of the "in situ" reaction. The colouring may be performed with natural extracts containing polyphenols and have a colouring close to henna without the inconvenient of the presence of naphtoquinones in such colourings. Another advantage lies in reactions like some enzymes without the problems associated with their uses in the cosmetic and dermatologic fields.

In the more biological field, the vectorization of such active ingredients is easier due to the size and the significantly inferior toxicological hazard than the use of proteins. The half-life of such a blend is probably higher than a protein which would be subjected, without a previous immobilization, to a quick degradation by the tissue proteases.

The use of a tanning composition for bath offers the interest to avoid for the consumer to be exposed for a long period to UV in order to reach a result (the association with a strongly screening formulation is therefore possible and ensures a more efficient safety towards UV).

The use of sodium hydrogenocarbonate does not seem to exhibit toxicological hazards (authorized use in the cosmetic industry) and the manganese amount is extremely low. For example, for a bath with a green tea extract (100 g), 20 g sodium hydrogenocarbonate and 100 mg manganese chloride, i.e. a [Mn(II)]/[HCO$_3$] ratio in the order of 1/500, are sufficient to have a colour development in a 100 liter bath. Some natural extracts (for example tea extract) contain Mn(II) and, in such a case, it will be sufficient to adapt the formulation posology depending on the Mn(II) content of the natural extract.

What is claimed is:

1. A composition comprising,
at least one colouring agent precursor comprising at least one aromatic cycle having at least two hydroxy groups bonded to two consecutive carbon atoms of the aromatic cycle, and optionally comprising at least one amino acid comprising at least one thiol group, and
a catalytic system comprising a first component selected from the group consisting of salts of Mn(II), oxides of Mn(II), salts of Zn(II), oxides of Zn(II) and mixtures thereof, and a second component selected from the group consisting of alkaline hydrogenocarbonates, alkaline earth hydrogenocarbonates and mixtures thereof,
in a physiologically acceptable medium, wherein the proportions of the first component and the second component in the catalytic system meet formulas (I)–(III)

$$\frac{[Mn(II)]}{[HCO_3]} \leq 1 \quad \text{with} \quad [Mn(II)] \neq 0$$

$$\frac{[Zn(II)]}{[HCO_3]} \leq 1 \quad \text{with} \quad [Zn(II)] \neq 0$$

$$\frac{[Mn(II) + Zn(II)]}{[HCO_3]} \leq 1 \quad \text{with} \quad [Mn(II)] \text{ and } [Zn(II)] \neq 0$$

where [Mn(II)], [Zn(II)] and [HCO$_3$] represent respectively the Mn(II), Zn(II) and HCO$_3$ molar concentrations in the composition.

2. The composition according to claim 1, wherein the [Mn(II)]/[HCO$_3$] ratio is from $10^{-5}$ to $10^{-1}$.

3. The composition according to claim 1, wherein the [Zn(II)]/[HCO$_3$] ratio is from $10^{-4}$ to <1.

4. The composition according to claim 1, wherein the [Mn(II)+Zn(II)]/[HCO$_3$] ratio is from $10^{-5}$ to $10^{-1}$.

5. The composition according to claim 1, wherein the Mn(II) and Zn(II) salts are selected from the group consisting of chloride, fluoride, iodide, sulfate, phosphate, nitrate, perchlorate, carboxylic acid salts and mixtures thereof.

6. The composition according to claim 5, wherein the Mn(II) and/or Zn(II) salt is a chloride.

7. The composition according to claim 6, wherein the carboxylic acid salts are hydroxylated carboxylic acid salts.

8. The composition according to claim 7, wherein the hydroxylated carboxylic acid salt is a gluconate.

9. The composition according to claim 1, wherein the hydrogenocarbonate is selected from the group consisting of sodium hydrogenocarbonate, potassium hydrogenocarbonate, magnesium hydrogenocarbonate, calcium hydrogenocarbonate and mixtures thereof.

10. The composition according to claim 1, wherein the aromatic cycle is a benzene cycle or a condensed aromatic cycle.

11. The composition according to claim 10, wherein the colouring agent precursor is a compound of formula:

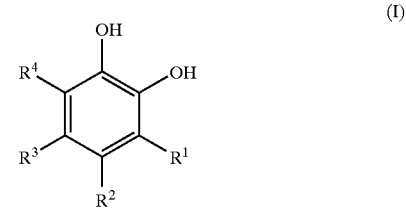

(I)

where $R^1$ to $R^4$ may be identical or different and represent a hydrogen atom, a halogen, hydroxyl, carboxyl, alkyl carboxylate radical, an optionally substituted amino radical, a linear or branched optionally substituted alkyl radical, a linear or branched optionally substituted alcenyl radical, a optionally substituted cycloalkyl radical, an alkoxy, alkoxyalkyl, alkoxyaryl radicals wherein the aryl group may be optionally substituted, aryl, substituted aryl, an optionally substituted heterocyclic radical, a radical containing one or more silicon atoms, where two of the components $R^1$ to $R^4$ jointly form a saturated or unsaturated cycle optionally containing one or more heteroatoms and optionally condensed with one or more saturated or unsaturated cycles optionally containing one or more heteroatoms.

12. The composition according to claim 1, wherein the colouring agent precursor is selected from the group consisting of flavanols, anthocyanidines, anthocyanines, hydroxybenzoates, flavones, iridoids, osylated iridoids, oligomeric iridoids, hydroxystilbenes, osylated hydroxystilbenes, 3,4-dihydroxy-phenylalanine, derivatives of 3,4-dihydroxy-phenylalanine, 2,3-dihydroxyphenylalanine, derivatives of 2,3-dihydroxyphenylalanine, 4,5-dihydroxyphenylalanine, derivatives of 4,5-dihydroxyphenylalanine, 4,5-dihydroxyindole. derivatives of 4,5-dihydroxyindole, 5,6-dihydroxyindole, derivatives of 5,6-dihydroxyindole, 6,7-dihydroxyindole, derivatives of 6,7-dihydroxyindole, 2,3-dihydroxyindole, derivatives of 2,3-dihydroxyindole, dihydroxycinnamates, hydroxycoumarins, hydroxyisocoumarins, hydroxycoumarones, hydroxyisocoumarones, hydroxychalcones, hydroxychromones, anthocyans, quinones, hydroxyxanthones and mixtures thereof.

13. The composition according to claim 1, wherein the colouring agent precursor is selected from the group consisting of plant extracts, fruit extracts, citrus fruit extracts, vegetable extracts and mixtures thereof.

14. The composition according to claim 13, wherein the colouring agent precursor is selected from the group consisting of tea extracts, grape extracts, apple extracts, banana extracts, potato extracts and mixtures thereof.

15. The composition according to claim 1, wherein the colouring agent precursor is present in an amount of at least 10 micromoles per milliliter.

16. The composition according to claim 1, comprising the amino acid, wherein the amino acid is an amino acid with an amine function in an α position relative to a carboxylic acid function.

17. The composition according to claim 16, wherein the amino acid is selected from the group consisting of cysteine, derivatives of cysteine, glutathione, and derivatives of glutathione.

18. The composition according to claim 1, wherein an amino acid with a thiol group/coloring agent precursor molar ratio is from 0.001 to 50.

19. The composition according to claim 1, wherein the colouring agent precursor is a dihydroxyphenylalanine or a dihydroxyindole, and the amino acid is cysteine or glutatione.

20. The composition according to claim 1, wherein the physiologically acceptable medium is a solubilizing medium of the colouring agent precursor and the amino acid.

21. The composition according to claim 1, wherein the physiologically acceptable medium comprises a solvent or a mixture of solvents of the colouring agent precursor and the amino acid.

22. The composition according to claim 21, wherein the solvent is selected from the group consisting of water, alcohols, ethers, dimethylsulfoxide, N-methylpyrrolidone, ketones and mixtures thereof.

23. The composition according to claim 22, wherein the alcohol is an alcanol or an alcanediol.

24. The composition according to claim 22, wherein the solvent is a water/alcohol mixture.

25. The composition according to claim 24, wherein the alcohol represents 80% wt of the mixture.

26. The composition according to claim 1, wherein no chelating agent of a Mn(II) and/or a Zn(II) salt is present.

27. The composition according to claim 1, comprising two separate components, wherein a first component comprises the catalytic system dissolved in a physiologically acceptable medium and a second component comprises the colouring agent precursor and optionally the amino acid having a thiol group dissolved in a physiologically acceptable medium.

28. The composition according to claim 1, wherein the composition is packed in the form of an aerosol or a pump system with no air absorption.

29. The composition according to claim 27, wherein the composition is packed in a pump system with two discrete compartments, each of the components contained separately in one of the two compartments.

30. The composition according to claim 1, wherein the composition is packed in the form of a shingle.

31. The composition according to claim 30, wherein the shingle comprises an excipient comprising citric and/or tartaric acid in a sub-stoichiometric amount relative to the alkaline and/or alkaline earth hydrogenocarbonate.

32. The composition according to claim 1, wherein the composition is packed in the form of two shingles, wherein a first shingle comprises the catalytic system and an excipient and a second shingle comprises the colouring agent precursor, the amino acid with an optional thiol group, and an excipient.

33. The composition according to claim 30, wherein the shingle is an effervescent shingle.

34. A method for revealing the colouring of a basic composition, comprising, adding to the basic composition, in the presence of oxygen, a catalytic system comprising a first component selected from the group consisting of salts of Mn(II), oxides of Mn(II), salts of Zn(II), oxides of Zn (II) and mixtures thereof, and a second component selected from the group consisting of alkaline hydrogenocarbonates, alkaline earth hydrogenocarbonates and mixtures thereof, wherein the proportions of the first component and the second component of the catalytic system meet formulas (I)–(III)

$$\frac{[Mn(II) + Zn(II)]}{[HCO_3]} \leq 1 \quad \text{with} \quad [Mn(II)] \text{ and } [Zn(II)] \neq 0 \quad \text{(III)}$$

$$\frac{[Mn(II)]}{[HCO_3]} \leq 1 \quad \text{with} \quad [Mn(II)] \neq 0 \quad \text{(I)}$$

$$\frac{[Zn(II)]}{[HCO_3]} \leq 1 \quad \text{with} \quad [Zn(II)] \neq 0 \quad \text{(II)}$$

where [Mn(II)], [Zn(II)] and [HCO$_3$] represent respectively the Mn(II), Zn(II) and HCO$_3$ molar concentrations in the composition, wherein the basic composition comprises at least one coloring agent having at least two hydroxyl groups bonded to two consecutive carbon atoms of an aromatic cycle and optionally at least one amino acid comprising at least one thiol group.

35. The method according to claim 34, wherein the [Mn(II)]/[HCO$_3$] ratio is from $10^{-4}$ to $10^{-1}$.

36. The method according to claim 34, wherein the [Zn(II)]/[HCO$_3$] ratio is from $10^{-4}$ to <1.

37. The method according to claim 34, wherein the [Mn(II)+Zn(II)]/[HCO$_3$] ratio is from $10^{-5}$ to $10^{-1}$.

38. The method according to claim 34, wherein the Mn(II) and Zn(II) salts are selected from the group consisting of chloride, fluoride, iodide, sulfate, phosphate, carboxylic acid salts and mixtures thereof.

39. The method according to claim 34, wherein the Mn(II) and/or Zn(II) salt is a chloride.

40. The method according to claim 38, wherein the carboxylic acid salts are hydroxylated carboxylic acid salts.

41. The method according to claim 40, wherein the hydroxylated carboxylic acid salt is a gluconate.

42. The method according to claim 34, wherein the hydrogenocarbonate is selected from the group consisting of sodium hydrogenocarbonate, potassium hydrogenocarbonate, magnesium hydrogenocarbonate, calcium hydrogenocarbonate and mixtures thereof.

43. The method according to claim 34, wherein the aromatic cycle is a benzene cycle or a condensed aromatic cycle.

44. The method according to claim 34, wherein the colouring agent precursor is a compound of formula:

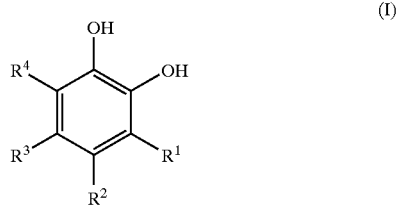

(I)

where R$^1$ to R$^4$ may be identical or different and represent a hydrogen atom, a halogen, a hydroxyl, carboxyl, alkyl carboxylate radical, an optionally substituted amino radical, a linear or branched optionally substituted alkyl radical, a linear or branched optionally substituted alcenyl radical, a optionally substituted cycloalkyl radical, an alkoxy, alkoxyalkyl, alkoxyaryl wherein the aryl group may be optionally substituted, aryl, substituted aryl, an optionally substituted heterocyclic radical, a radical containing one or more silicon atoms wherein two of the components R$^1$ to R$^4$ jointly form a saturated or unsaturated cycle optionally containing one or more heteroatoms and optionally condensed with one or more saturated or unsaturated cycles optionally containing one or more heteroatoms.

45. The method according to claim 34, wherein the colouring agent precursor is selected from the group consisting of flavanols, anthocyanidines, anthocyanines, hydroxybenzoates, flavones, iridoids, osylated iridoids, oligomeric iridoids, hydroxystilbenes, osylated hydroxystilbenes, 3,4-dihydroxyphenylalanine, derivatives of 3,4-dihydroxyphenylalanine, 2,3-dihydroxyphenylalanine, derivatives of 2,3-dihydroxyphenylalanine, 4,5-dihydroxyphenylalanine, derivatives of 4,5-dihydroxyphenylalanine, 4-5-dihydroxyindole derivatives of 4-5-dihydroxyindole, 5,6-dihydroxyindole, derivatives of 5,6-dihydroxyindole, 6,7-dihydroxyindole, derivatives of 6,7-dihydroxyindole, 2,3-dihydroxyindole, derivatives of 2,3-dihydroxyindole, dihydroxycinnamates, hydroxycoumarins, hydroxyisocoumarins, hydroxycoumarones, hydroxyisocoumarones, hydroxychalcones, hydroxychromones, anthocyans, quinones, hydroxyxanthones and mixtures thereof.

46. The method according to claim 34, wherein the colouring agent precursor is selected from the group consisting of plant extracts, fruit extracts, citrus fruit extracts, vegetable extracts and mixtures thereof.

47. The method according to claim 46, wherein the coloring agent precursor is selected from the group consisting of tea extracts, grape extracts, apple extracts, banana extracts, potato extracts and mixtures thereof.

48. The method according to claim 34, wherein the colouring agent precursor is present in an amount of at least 10 micromoles per milliliter.

49. The method according to claim 34, wherein the amino acid comprising at least one thiol group is an amino acid with an amine function in an α position relative to a carboxylic acid function.

50. The method according to claim 49, wherein the amino acid is selected from the group consisting of cysteine, derivates of cysteine, glutathione and derivates of glutathione.

51. The method according to claim 34, wherein the amino acid with a thiol group/coloring agent precursor molar ratio is from 0.01 to 5.

52. The method according to claim 34, wherein the physiologically acceptable medium is a solubilizing medium of the colouring agent precursor and the amino acid with a thiol group.

53. The method according to claim 34, wherein the physiologically acceptable medium comprises a solvent or a mixture of solvents of the colouring agent precursor and/or the amino acid with a thiol group.

54. The method according to claim 53, wherein the solvent is selected from the group consisting of desalted water, alcohol, ethers, dimethylsulfoxide, N-methylpyrrolidone, ketones and mixtures thereof.

55. The method according to claim 54, wherein the alcohol is an alcanol or an alcanediol.

56. The method according to claim 55, wherein the solvent is a desalted water/alcohol mixture.

57. The method according to claim 56, wherein the alcohol is up to 80% wt of the mixture.

58. The method according to claim 34, wherein no chelating agent of a Mn(II) and/or a Zn(II) salt is present.

59. A method for obtaining a colouring composition, comprising
adding to water a shingle comprising the colouring agent precursor of claim 1 and optionally at least one amino acid comprising at least one thiol group, one or more alkaline or alkaline earth hydrogenocarbonates and optionally at least one salt of Mn(II) and/or Zn(II) oxide wherein $$\frac{[Mn(II) \text{ and/or } Zn(II)]}{[HCO_3]} \leq 1 \text{ with } [Mn(II)] \text{ and/or } [Zn(II)] \neq 0.$$

60. A method for obtaining a colouring composition, comprising
adding to water a first shingle comprising a colouring agent precursor and optionally at least one amino acid comprising at least one thiol group, and a second shingle comprising a catalytic system, the precursor, the amino acid and the catalytic system of claim 1 in a physiologically acceptable medium.

61. The method according to claim 59, wherein the shingles are effervescent shingles.

62. A method for colouring skin and/or keratin matters, comprising
applying on skin and/or on keratin matters a layer of the composition according to claim 1.

63. The method according to claim 62, wherein the layer is obtained by applying on skin and/or on keratin matters a first film of a basic composition comprising the colouring agent precursor and optionally the amino acid comprising at least one thiol group in a physiologically acceptable medium, and applying on the first film a second film of a catalytic composition comprising the catalytic system in a physiologically acceptable medium.

64. The method according to claim 62 wherein the films are applied by spraying.

65. The composition of claim 2, wherein the [Mn(II)]/[HCO$_3$] ratio is from $10^{-3}$ to $10^{-2}$.

66. The composition of claim 2, wherein the [Mn(II)]/[HCO$_3$] ratio is in the order of $5 \times 10^{-3}$.

67. The composition of claim 3, wherein the [Zn(II)]/[HCO$_3$] ratio is from $10^{-3}$ to less than 1.

68. The composition of claim 3, wherein the [Zn(II)]/[HCO$_3$] is in the order $5 \times 10^{-1}$.

69. The composition of claim 4, wherein the [Mn(II)+Zn(II)]/[HCO$_3$] ratio is from $10^{-3}$ to $10^{-2}$.

70. The composition of claim 18, wherein the amino acid with a thiol group/colouring agent precursor molar ratio is from 0.01 to 5.

71. The composition of claim 18, wherein the amino acid with a thiol group/colouring agent precursor molar ratio is from 0.05 to 2.5.

72. The composition of claim 20, wherein the physiologically acceptable medium has a bacteriostatic property.

73. The composition of claim 25, wherein the alcohol is from 1 to 50 wt % of the mixture.

74. The composition of claim 25, wherein the alcohol is from 5 to 20 wt % of the mixture.

75. The method according to claim 35, wherein the [Mn(II)]/[HCO$_3$] ratio is from $10^{-3}$ to $10^{-2}$.

76. The method of claim 35, wherein the [Mn(II)]/[HCO3] ratio is in the order $5 \times 10^{-3}$.

77. The method according to claim 36, wherein the [Zn(II)]/[HCO$_3$] ratio is from $10^{-3}$ to less than 1.

78. The method of claim 36, wherein the [Zn(II)]/[HCO$_3$] ratio is in the order $5 \times 10^{-1}$.

79. The method of claim 37, wherein the [Mn(II)+Zn(II)]/[HCO$_3$] ratio is from $10^{-3}$ to $10^{-2}$.

80. The method of claim 51, wherein the amino acid with a thiol group/colouring agent precursor molar ratio is from 0.5 to 2.5.

81. The method according to claim 52, wherein the physiologically acceptable medium has a bacteriostatic property.

82. The method of claim 57, wherein the alcohol is from 1 to 50 wt % of the mixture.

83. The method according to claim 57, wherein the alcohol is from 5 to 20 wt % of the mixture.

84. The method according to claim 62, wherein the layer is obtained by applying on skin and/or on keratin matters a first film of a catalytic composition comprising the catalytic system in a physiologically acceptable medium, and applying on the first film a second film of a basic composition containing the coloring agent precursor and optionally the amino acid comprising at least one thiol group in a physiologically acceptable medium.

85. The method according to claim 62 wherein the films are applied by spraying.

86. The method according to claim 60, wherein the shingles are effervescent shingles.

87. The composition according to claim 32, wherein the shingle is an effervescent shingle.

* * * * *